(12) United States Patent
Barry et al.

(10) Patent No.: US 6,663,606 B1
(45) Date of Patent: *Dec. 16, 2003

(54) BIOCOMPATIBLE MEDICAL DEVICES

(75) Inventors: James Barry, Marlborough, MA (US); Maria Palasis, Wellsley, MA (US); Louis Ellis, St. Anthony, MN (US); Timothy Mickley, Elk River, MN (US); Brian Berg, St. Paul, MN (US); Justin Crank, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,586

(22) Filed: Feb. 14, 2000

Related U.S. Application Data

(63) Continuation-in-part of application No. 09/429,178, filed on Oct. 28, 1999.

(51) Int. Cl.⁷ .......................... A61M 25/00; A61M 5/32
(52) U.S. Cl. ........................... 604/264; 604/272
(58) Field of Search ................ 604/264, 265, 604/266, 890.1, 891.1, 272; 623/1.44, 1.45, 1.46; 427/2.12, 2.25

(56) References Cited

U.S. PATENT DOCUMENTS 2,814,296 A * 11/1957 Everett ...................... 604/265
3,358,684 A * 12/1967 Marshall ..................... 604/265

(List continued on next page.)

FOREIGN PATENT DOCUMENTS

| EP | 0 798 398 A2 | 10/1997 | ............. C23C/8/38 |
|----|---|---|---|
| WO | WO 92/05829 | 4/1992 | .......... A61M/29/00 |
| WO | WO 94/16836 | 8/1994 | ............. B08B/3/12 |
| WO | WO 98/40469 | 9/1998 | ............. C12N/5/12 |
| WO | WO 98/53762 | 12/1998 | ............. A61F/2/06 |
| WO | WO 99/22655 | 5/1999 | .......... A61B/17/32 |
| WO | WO 99/62395 | 12/1999 | |
| WO | WO 00/76573 A1 | 12/2000 | .......... A61M/31/00 |

OTHER PUBLICATIONS

"Standard Specification for Chemical Passivation Treatments for Stainless Steel Parts", American Society For Testing And Materials, Designation A 967–96, pp. 1–6.

*Primary Examiner*—Sharon Kennedy
(74) *Attorney, Agent, or Firm*—Mayer Fortkort & Williams, PC; David B. Bonham, Esq.

(57) ABSTRACT

A modified medical device for delivery of a pharmaceutically active material is described. The present inventors have found that many conventional medical devices contain a metallic or polymeric component that comes into contact with a pharmaceutically active material during use, and that the contact substantially reduce the pharmaceutical effectiveness of the pharmaceutically active material. The invention described herein concerns various modifications to the metallic or polymeric component that are effective to diminish such a substantial reduction in pharmaceutical effectiveness.

34 Claims, 13 Drawing Sheets

U.S. PATENT DOCUMENTS

| | | | |
|---|---|---|---|
| 3,598,127 A | * 8/1971 | Wepsic | 604/265 |
| 4,589,873 A | * 5/1986 | Schwartz et al. | 604/265 |
| 4,838,877 A | 6/1989 | Massau | 604/272 |
| 4,999,210 A | * 3/1991 | Solomon et al. | 427/2 |
| 5,098,977 A | 3/1992 | Frautschi et al. | 527/313 |
| 5,266,359 A | 11/1993 | Spielvogel | 427/388.4 |
| 5,368,048 A | 11/1994 | Stoy et al. | 128/772 |
| 5,385,152 A | * 1/1995 | Abele et al. | 128/772 |
| 5,468,562 A | * 11/1995 | Farivar et al. | 428/457 |
| 5,492,763 A | * 2/1996 | Barry et al. | 428/457 |
| 5,584,821 A | * 12/1996 | Hobbs et al. | 604/280 |
| 5,607,401 A | 3/1997 | Humphrey | 604/239 |
| 5,637,399 A | 6/1997 | Yoshikawa et al. | 428/369 |
| 5,643,255 A | * 7/1997 | Organ | 606/41 |
| 5,671,754 A | 9/1997 | Schmukler et al. | 128/844 |
| 5,891,507 A | * 4/1999 | Jayaraman | 427/2.25 |
| 5,928,216 A | * 7/1999 | Spencer | 604/523 |
| 5,997,517 A | * 12/1999 | Whitbourne | 604/265 |
| 6,059,738 A | 5/2000 | Stoltze et al. | 600/585 |
| 6,096,070 A | * 8/2000 | Ragheb et al. | 623/1 |
| 6,103,037 A | * 8/2000 | Wilson | 156/158 |
| 6,120,536 A | 9/2000 | Ding et al. | 623/1.43 |

* cited by examiner

BIOCOMPATIBLE MEDICAL DEVICES

STATEMENT OF RELATED APPLICATION

This is a continuation-in-part of U.S. Ser. No. 09/429,178 filed Oct. 28, 1999 and entitled "Biocompatible Medical Devices".

FIELD OF THE INVENTION

The present application relates to medical devices for delivery of pharmaceutically active materials. More specifically, the present invention relates to methods and compositions effective to prevent reduction in the activity of pharmaceutically active materials arising from contact with metallic or polymeric components of medical devices.

BACKGROUND OF THE INVENTION

Medical devices having metallic and polymeric components are used extensively in the medical field. In many cases the medical device is used for delivery of a pharmaceutically active material, and the pharmaceutically active material comes into contact with the metallic or polymeric component during the course of delivery of the pharmaceutically active material.

For example, metallic lumens are frequently used to carry pharmaceutically active materials to various bodily tissues. As another example, metallic stents having a drug delivery polymer coating thereon are used for delivery of pharmaceutically active materials. In both examples, the pharmaceutically active material contacts the metallic component. Metallic components such as stainless steel and nickel-titanium superelastic alloys (e.g., nitinol), cobalt based alloys and super-alloys are commonly used for this purpose as they are formable, have desirable mechanical properties and are commonly believed to be substantially inert.

Moreover, polymeric materials such as polycarbonate, polyimide, acrylonitrile/butadiene/styrene resins (ABS), poly ether ether ketone (PEEK), epoxy and nylon also commonly contact pharmaceutically active materials in connection with their use as catheters, stents, manifolds, stopcocks, needle materials, and so forth.

The present inventors, however, have found that such materials are relatively incompatible with certain pharmaceutically active materials. As a result, there is at present a need in the art to overcome this incompatibility.

Viral solution is pushed through the catheters and analyzed at 5, 10, 15, 20 and 25 minutes.

Figure 11:
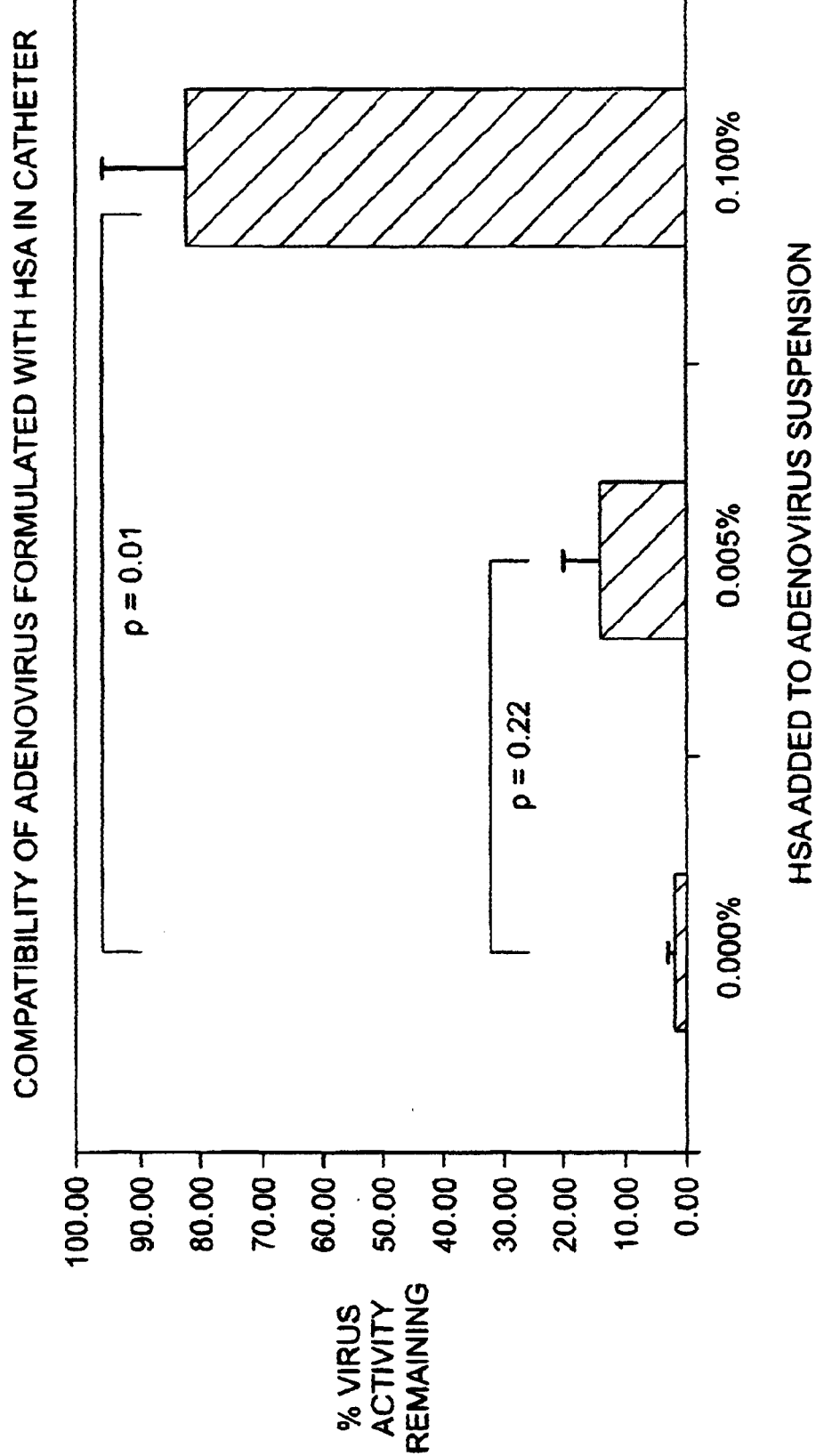

FIG. 11 presents virus titer as a percentage of viral stock titer (linear scale) for adenoviral solutions containing HSA concentrations of 0% (no HSA addition), 0.005% and 0.1%, after incubation within a need injection catheter for 30 minutes.

Figure 12:
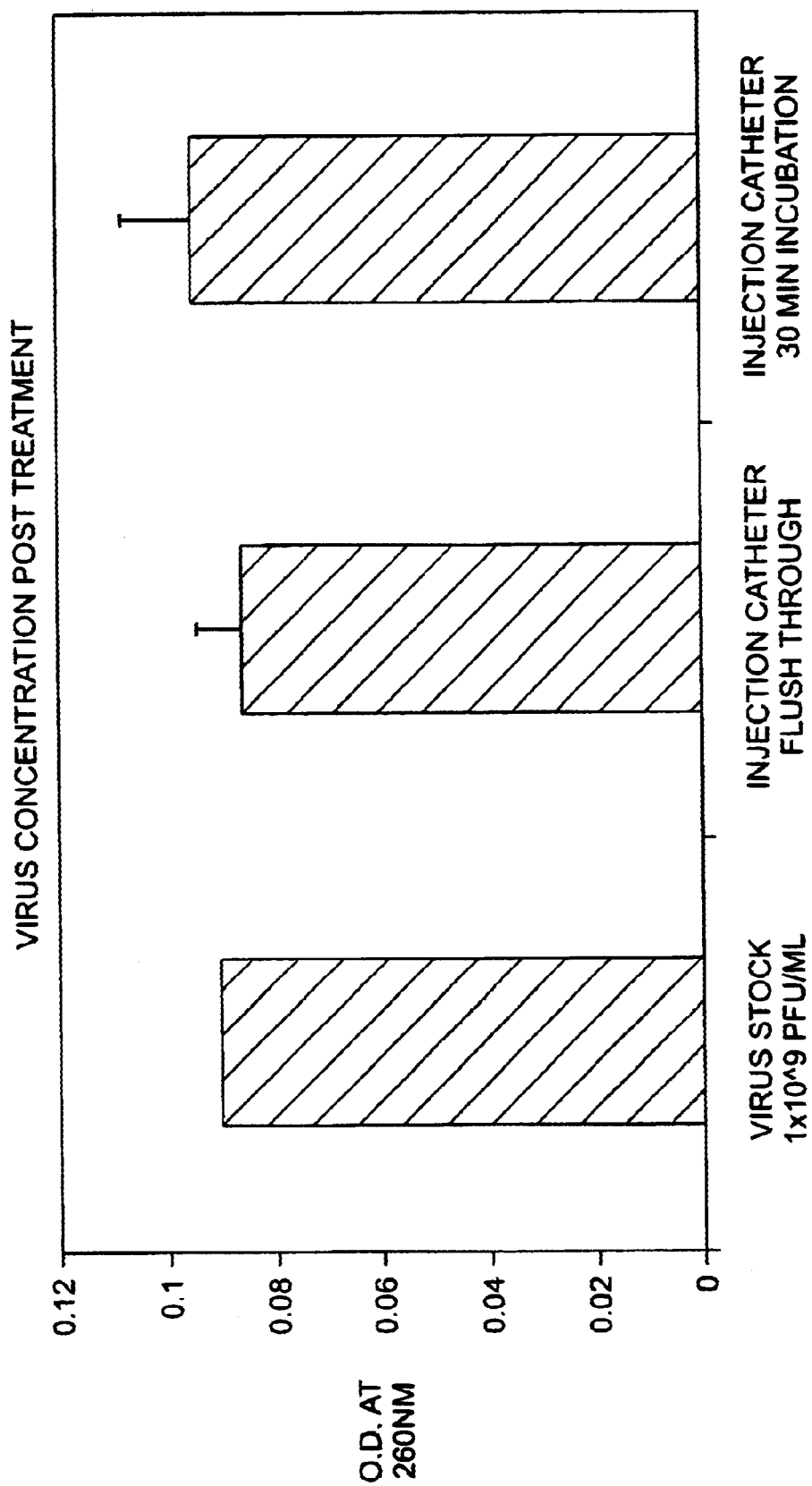

FIG. 12 presents OD 260 data for (a) virus stock, (b) virus stock after flushing through an injection catheter constructed of stainless steel and nitinol, and (c) virus stock after 30 minute incubation in an injection catheter constructed of stainless steel and nitinol.

Figure 13:
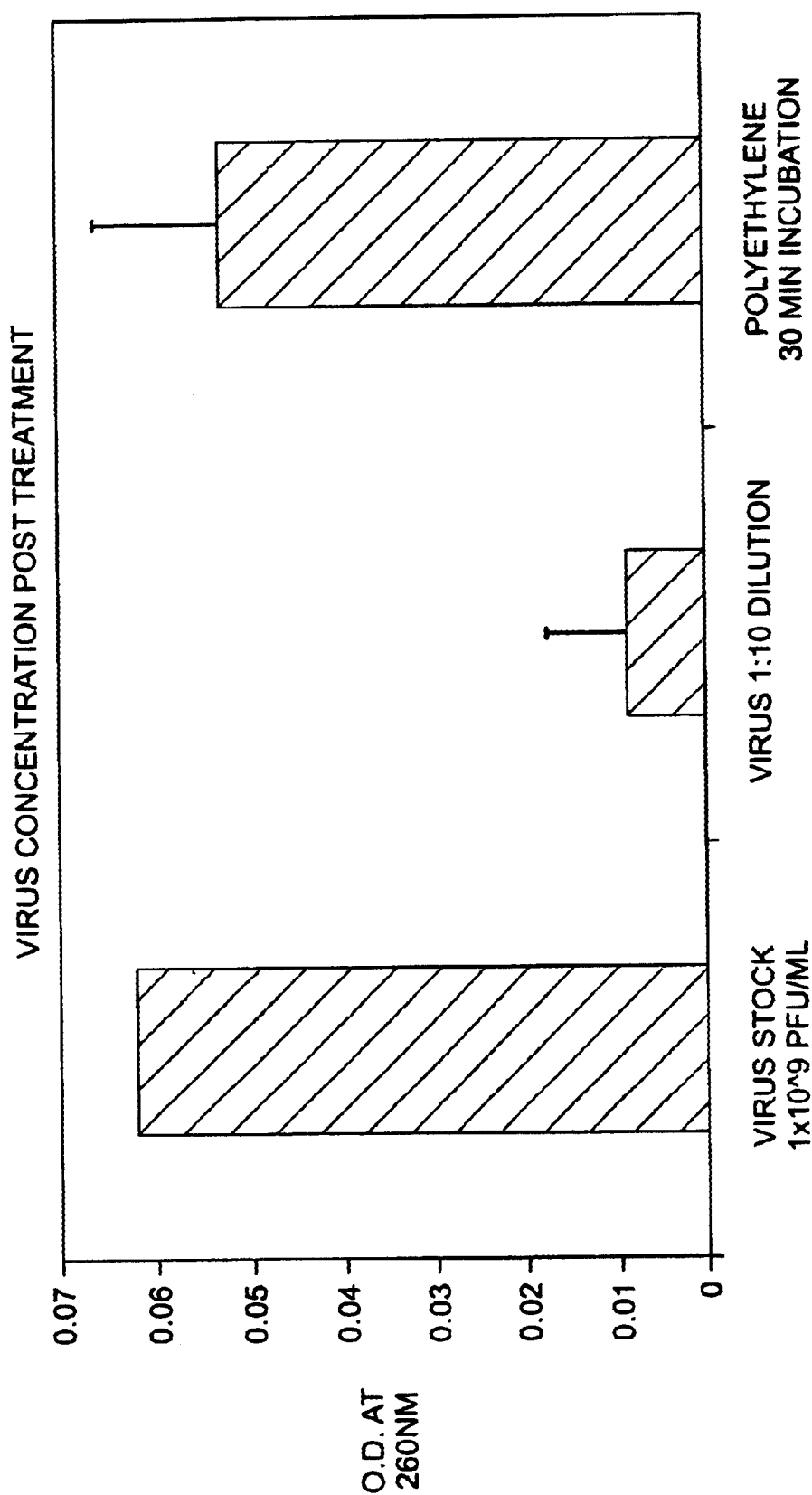

FIG. 13 presents OD 260 data for (a) virus stock (b) virus stock after 1:10 dilution, and (c) virus stock after 30 minutes incubation in a polyethylene lumen.

SUMMARY OF THE INVENTION

According to an embodiment of the invention, a method and modified medical device for delivery of a pharmaceutically active material are provided. The medical device comprises a conventional medical device having a metallic or polymeric component that comes into contact with a pharmaceutically active material, such as a viral vector, during use, such contact acting to substantially reduce the pharmaceutical effectiveness of the pharmaceutically active material. The conventional medical device is thus said to be "incompatible" with the pharmaceutically active material. The incompatible metallic or polymeric component is modified to prevent this substantial reduction in pharmaceutical effectiveness in accordance with the invention.

Numerous devices benefit from the present invention, including medical devices comprising a metallic lumen, such as hypodermic needles and intravascular catheters having an injection lumen, and medical devices that do not have a lumen, such as metallic stents coated with polymer for delivery of the pharmaceutically active material. Examples of metallic components resulting in a substantial reduction in pharmaceutical effectiveness include stainless steel and nitinol. Examples of incompatible polymeric components include polycarbonate, polyimide, acrylonitrile/butadiene/styrene resins (ABS), poly ether ether ketone (PEEK), epoxy and nylon.

Pharmaceutically active materials appropriate for the practice of the present invention are those that benefit from the present invention and include materials comprising polynucleotides, in conjunction with viral or non-viral vectors, proteins, small and large molecule drugs, and so forth.

According to one aspect of the invention, the incompatible polymeric or metallic component is modified by providing it with a surface treatment. Appropriate surface treatments include chemical passivation treatments, such as acid treatment (e.g., treatment with citric acid, nitric acid, etc.) and treatment with steam. Other appropriate surface treatments include treatment with a pharmaceutically acceptable protein, such as albumin, or treatment with a layer of more compatible polymeric material, such as polyethylene (high or low density), polypropylene, polytetrafluoroethylene (PTFE), poly(tetrafluoroethylene-co-exafluoropropene) (FEP), modified ethylene-tetrafluoroethylene copolymer (ETFE), polyvinylidene fluoride (PVDF), polyethylene terephthalate polyester (PET-P) and so forth. In some embodiments, the polymer is provided as a preformed composition, in other embodiments, the polymer is applied in an uncured form, such as a liquid form, and cured. Still other appropriate surface treatments include treatment with a layer of inorganic material, such as carbon, for example, by means of chemical vapor deposition. Yet other surface treatments involve providing the incompatible metallic or polymeric component with a layer of a more inert metallic material, such as titanium or platinum.

In other embodiments, the incompatible metallic or polymeric component is replaced, for example, with a more compatible metallic or polymeric component, such as gold, titanium and platinum, or with a more compatible polymeric component, such as polyethylene (low or high density), polypropylene, polyethylene terephthalate polyester (PET-P), polyfluorocarbons (e.g., polytetrafluoroethylene (PTFE), modified ethylene-tetrafluoroethylene copolymer (ETFE), poly(tetrafluoroethylene-co-hexafluoropropene) (FEP), polyvinylidene fluoride (PVDF), and so forth), or with an inorganic material such as glass.

One advantage of the present invention is that incompatibility problems that are presently experienced when components of medical devices, including accessories, come into contact with pharmaceutically active materials are minimized.

Another advantage is that the pharmaceutical effectiveness of pharmaceutically active materials that come into contact with device components is not substantially decreased.

Still other embodiments and advantages will become readily apparent to those skilled in the art upon review of the Detailed Description, Examples and Claims set forth below.

DETAILED DESCRIPTION

At present, many medical devices are known in which pharmaceutically active materials pass through metallic or polymeric lumens or otherwise come into contact with metal or plastic prior to delivery to tissue. However, as seen from the examples below, the present inventors have found that where pharmaceutically active materials, specifically viral particles, contact certain metallic or polymeric substrates, including adhesives, pharmaceutical effectiveness is substantially reduced relative to the same materials, which have not come into contact with such substrates. Specifically, the present inventors have found that where pharmaceutically active materials such as viral particles contact metallic materials, such as stainless steel and/or nickel-titanium superalloys such as nitinol, or polymeric materials such as PEEK, polyimide, epoxy, nylon, ABS and/or polycarbonate, viral transfection is substantially reduced, apparently due to inactivation of the virus. This is surprising, since it is normally assumed that such materials are relatively inert and hence unlikely to interact with a pharmaceutically active material.

By "substantially reduced" or "substantial reduction" is meant that pharmaceutical effectiveness is reduced, for example, by at least 5%, more commonly 10%, 20%, 30%, 40%, 50% or more. By "pharmaceutical effectiveness" or "pharmaceutical efficacy" is meant any desired pharmaceutical pharmacological result. For example, a virus having a 10% reduction in pharmaceutical effectiveness is able to infect 10% less cells than it otherwise would. As another example, the pharmaceutical effectiveness of a protein can be measured by its activity through an ELISA assay.

Polymeric or metallic components resulting in such a substantial reduction are referred to herein as "incompatible metallic or polymeric components". Conversely, components that diminish such a reduction in pharmaceutical effectiveness are referred to herein as "more compatible" components.

The present invention overcomes the above and other difficulties by providing medical devices for delivery of pharmaceutically active materials in which the incompatible metallic and/or polymeric components of such devices (including adhesives) that come into contact with the pharmaceutically active materials are modified or replaced with a more compatible component. The devices of the present invention thus do not result in a substantial reduction in pharmaceutical effectiveness.

Conventional (i.e., known) medical devices benefiting from the present invention are numerous and include, for example, catheters, conventional needle syringes, hypodermic needles, biopsy needles and devices, tissue ablation devices, needle injection catheters (for endocardial, epicardial, and pericardial agent administration), filters, grafts, metallic and polymeric stents including those having a polymer coated thereon for delivery of pharmaceutically active materials, aneurysm filling coils, transmyocardial revascularization devices, percutaneous myocardial revascularization devices, soft tissue clips, sutures, blood clot filters, implants or spikes (polymeric or metallic), microspheres or nanoparticles, and so forth. Specific examples of devices for drug delivery to the heart include, for example, those found in the following patents and patent applications: U.S. Pat. Nos. 5,450,846, 5,840,059, 5,878,751, 5,551,427, 5,931,834, 5,925,012, 5,925,033, 5,538,504, WO 99/39624, WO 99/44656, WO 99/21510, WO 99/29251, EP A 99-06 0895752, and EP A 99-01 0888750, each of which is incorporated herein by reference. Components of medical devices benefiting from the present invention are numerous and include, for example, adhesives, coatings, balloons, membranes, manifolds, hubs, fittings, etc. Accessory components used in conjunction with medical devices also benefiting from the present invention and include stopcocks, valves, tubing kits, manifolds, wires, syringes, etc.

The medical devices contemplated for use in connection with the present invention can be used for systemic treatment or to treat any mammalian tissue or organ. Non-limiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone. The terms "pharmaceutically active materials", "therapeutic agents" and "drugs" are used interchangeably herein and include pharmaceutically active compounds, polynucleotides with and without carrier vectors such as lipids, compacting agents (such as histones), viruses, virus-like particles (i.e., synthetic particles made to act like viruses), polymers, proteins, enzymes, small and large molecule drugs, and the like, with or without targeting sequences. An injection administered in accordance with the present invention includes the pharmaceutically active material and solutions thereof. Pharmaceutically active materials useful in accordance with the present invention may be used singly or in combination.

A "polynucleotide" is a nucleic acid molecule polymer, such as DNA, RNA and their analogs, having as few as 3 nucleotides, and can include both double- and single-stranded sequences. A "protein" is a polymer of as few as two (dimer) amino acid residues.

Preferably, the pharmaceutically active material is a polynucleotide, more preferably in conjunction with virus or virus-like particles. Specific examples of viruses include adenovirus, paroviruses such as adeno-associated virus, lentivirus, retrovirus, alpha-virus, papilloma virus, murine leukemia virus, Semliki Forest virus, etc.

Specific examples of pharmaceutically active materials used in conjunction with the present invention include, for example, pharmaceutically active compounds, proteins, oligonucleotides, ribozymes, antisense oligonucleotides, DNA compacting agents, gene/vector systems (i.e., any vehicle that allows for the uptake and expression of nucleic acids), polynucleotides (including, for example, recombinant nucleic acids; naked DNA, cDNA, or RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposome and cationic polymers that are selected from a number of types depending on the desired application.

Several therapeutic categories and exemplary pharmaceutically active materials follow. Examples include anti-inflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, rapamycin, epothilones, endostatin, angiostatin, thymidine kinase inhibitors, and analogues thereof; anesthetic agents such as lidocaine, bupivacaine, ropivacaine, and analogues thereof; anti-coagulants; integrins, chemokines, cytokines and growth factors.

According to one embodiment of the invention, an incompatible metallic or polymeric component of a medical device (including adhesives) is modified by providing it with a surface treatment. All methods of the present invention, including surface treatments, are carried out to prevent a substantial reduction in pharmaceutical efficacy of the pharmaceutically active material.

One form of surface treatment in accordance with the present invention is a chemical passivation treatment. Preferred chemical passivation treatments include those that provide a robust oxide barrier, such as acid treatment with or without treatment with steam at high temperature. Preferred acids for this purpose include citric acid, nitric acid, and chromic acid. According one preferred embodiment, an incompatible metallic component is treated with acid, immediately followed by treatment with steam at high temperature (e.g., by autoclaving). Information concerning chemical passivation of stainless steel can be found, for example, in ASTM Designation: A 967-96 entitled "Standard Specification for Chemical Passivation Treatments for Stainless Steel Parts," the entire disclosure of which is hereby incorporated by reference. Procedures are set forth therein for nitric acid treatment, citric acid treatment, as well as other treatments, including electrochemical treatments.

Other forms of surface treatment include treating the incompatible metallic or polymeric component with solutions containing lipids and liposomes; emulsifying agents and detergents such as glycerin, sodium lauryl sulfate, sodium oleate; proteins, such as, for example, albumin, particularly human serum albumin (HSA) and bovine serum albumin (BSA); other natural polymers such as hyaluronic acid, laminin, fibronectin, fibrin, and collagen, as well as glucans and glycosaminoglycans, such as dextrans, dextran sulfate and heparin; synthetic polymers such as polyethylene glycol, polyethylene oxide, polyvinyl pyrrolidone, SP 017

(Supratek Pharma), polyethylenimine, protamine sulfate, polyamidoamine dendrimers, amphiphilic peptides, RGD-oligolysine peptides, and fluorocarbons such as polytetrafluoroethylene; contrast agents such as iohexol, blood or serum, and so forth. Treatment may be carried out by contacting the agents mentioned above with the incompatible metallic or polymeric component before that component is brought into contact with the therapeutic agent. Treatment may also be carried out by formulating the agents mentioned above directly into the solution or suspension containing the therapeutic agent. For instance, human serum albumin may be formulated into a viral suspension such as adenovirus in order to exert a protective or stabilizing effect. Additionally, the surface treatment may concurrently involve a cleaning process and/or sterilization process to remove surface contaminants or impurities.

Still other forms of surface treatment involve formation of an inorganic layer, for example, amorphous carbon, other diamond-like coatings, or silicon carbide. A preferred method of forming such inorganic layers is chemical vapor deposition (CVD) or physical vapor deposition (PVD). The inorganic layer may also be glass. Surface modifications such as sintering are also possible.

In the case of certain polymeric and other materials of suitable mechanical character, the surface treatment may simply involve the application of a layer of preformed material. As an example, in the case of an incompatible metallic or polymeric lumen, the metallic or polymeric surface can be treated by simply inserting a preformed tube, for example, of a more compatible material into the incompatible metallic or polymeric lumen.

Moreover, polymers and other materials can be formed on the metallic or polymeric substrate by any suitable means, such as dipping, spraying, vapor deposition, plasma polymerization and so forth. In many embodiments, a liquid layer is solidified. For example, in the case of polymers, the incompatible metallic or polymeric surface can be treated by forming a polymer layer on the metallic or polymeric component from a liquid layer. Exemplary embodiments for the formation of polymer layers from a liquid layer include (a) formation of a solvent dispersion of a polymer of interest, then coating a surface of the metallic component with the dispersion, followed by removal of solvent, and (b) first coating a surface of the metallic component with a curable polymer resin and subsequently curing the resin, for example, with ultraviolet or infrared radiation.

Hence, polymers appropriate for the practice of the invention include preformed and unformed polymers or hydrogels. Polymers may be crosslinked or uncrosslinked, natural or synthetic, biostable, biodegradable, or dissolvable. These materials may be selected from numerous polymers known in the art. Exemplary polymers are selected from polycarboxylic acids, cellulosic polymers including cellulose acetate and cellulose nitrate, gelatin, polyvinylpyrrolidone, cross-linked polyvinylpyrrolidone, polyanhydrides including maleic anhydride polymers, polyvinyl alcohols, copolymers of vinyl monomers such as EVA (ethylene-vinyl acetate copolymer), polyvinyl ethers, polyvinyl aromatics, polyethylene oxides, glycosaminoglycans, polysaccharides, polyesters including polyethylene terephthalate, polyacrylamides, polyethers, polyether sulfone, polyalkylenes including polypropylene, polyethylene (low and high density) and high molecular weight polyethylene, ethylene vinyl acetate polymers, halogenated polyalkylenes including polytetrafluoroethylene (PTFE), poly(tetrafluoroethylene-co-hexafluoropropene) (FEP), modified ethylene-tetrafluoroethylene copolymer (ETFE), polyvinylidene fluoride (PVDF), and so forth, polyurethanes, polyorthoesters, proteins, polypeptides, silicones, styrene-butadiene polymers, polylactic acid, polyglycolic acid, polycaprolactone, polyhydroxybuterate valerate and blends and copolymers thereof as well as other biodegradable, bioabsorbable and biostable polymers and copolymers. Thermoplastic elastomers such as polyether block amides and styrene-butadiene-styrene are also contemplated. Coatings from polymer dispersions such as polyurethane dispersions (BAYHYDROL, etc.) and acrylic latex dispersions are also within the scope of the present invention. The polymer may be a protein polymer, fibrin, collagen, derivatives of these polysaccharides, an extra cellular matrix component, hyaluronic acid, or another biologic agent or a suitable mixture of any of these, for example. In one embodiment, the polymer is polyacrylic acid, available as HYDROPLUS (Boston Scientific Corporation, Natick Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another embodiment, the polymer is a copolymer of polylactic acid and polycaprolactone.

Preferred polymers include polyethylene (low or high density), polyethylene terephthalate polyester (PET-P), ethylene vinyl acetate polymers, polysulfone, high viscosity acetal homopolymer (such as DELRIN 100), polypropylene, silicone polymers, polyurethanes, styrene-butadiene polymers, polymers such as Poly Penco Ultem 1000 and Hydex 301 Isoplast, fluorinated polyalkenes such as polytetrafluoroethylene (PTFE), poly(tetrafluoroethylene-co-hexafluoropropene) (FEP), modified ethylene-tetrafluoroethylene copolymer (ETFE), polyvinylidene fluoride (PVDF), ethylene chlorotrifluoroethylene copolymer (ECTFE)(such as HALAR 500 HF), and so forth. More preferred polymers include polypropylene, polyethylene (low or high density), PET-P, and fluorinated polymers such as PTFE, ETFE, FEP, and PVDF.

In general, favorable interactions (e.g., ionic, van der Waals, hydrophobic, etc.) between the material and therapeutic agent should be reduced such as to avoid adsorption of the therapeutic agent onto the surface or inactivation or denaturation by the surface.

In other embodiments, the incompatible metallic or polymeric component is replaced with a more compatible component. Exemplary embodiments include replacement of the incompatible metallic or polymeric component with a polymeric component such as those previously discussed. As above, the polymer should be more compatible with the pharmaceutically active material and, of course, the subject into which the pharmaceutically active material is to be introduced. Moreover, the polymer should meet any structural requirements. Numerous methods are available to provide structural integrity or flexibility.

For example, in the event that the medical device comprises a needle (or cannula) for delivery of the pharmaceutically active material, a polymeric needle can be fashioned from several of the materials listed above, notably, PTFE, PET-P, polyphenylene sulfide (PPS), and polysulfone (PS), which have excellent rigidity and the ability to be sharpened into a needle. Additional materials are disclosed in U.S. Pat. No. 4,838,877, including, polyetherimides, polymethylpentenes, polyesters, acrylates, polyaramides, modified phenylene oxides, and polysulfones. Alternatively, where enhanced strength and/or rigidity are desired, the polymeric material can be reinforced, for example, by fibers. For example, U.S. Pat. No. 5,637,399 discloses a synthetic resin needle of reinforced with combustible fibers whose longitudinal directions are arrayed straight or curvilinearly along the axial length of the needle. Numerous resins are listed, from which one or ordinary skill in that art can select and test for compatibility, for example, using the procedures set forth in the Examples. Metal or ceramic reinforcements may be included in addition to combustible fibers.

In still other embodiments, an incompatible metallic or polymeric component is replaced or coated with a more compatible metal. For example, stainless steel or nickel-titanium alloys (e.g. nitinol) may be coated with gold, titanium or platinum. Alloys may also be replaced with pure metals. In still other embodiments, an incompatible metallic or polymeric component is replaced or coated with silica materials or fibers, such as glass or quartz.

Glass or quartz materials appropriate for the practice of the invention include fused silica fibers. Such fused silica fibers are flexible and do not take on a set shape after being bent for a given period of time. According to one embodiment, a lumen made of fused silica fibers can be formed. In certain embodiments, such a lumen of fused silica fibers can be inserted into another outer lumen material, such as a metal lumen or a plastic lumen, which outer lumen would provide additional properties such as stiffness, bonding, color, friction resistance (e.g., PTFE), and so forth. In this way, the pharmaceutically active material that travels through the lumen contacts only the fused silica.

In the case of adhesives, for instance, an incompatible adhesive may be replaced with a more compatible one. For example, as seen in the Examples below, a virally incompatible adhesive, such as FDA2 or FDA23 (epoxy-based adhesives) can be replaced with a more compatible one, such as HB Fuller 3507 (a urethane-based adhesive). As an alternative example, the incompatible adhesive is coated with a more compatible polymer material.

Below are examples of specific embodiments for carrying out the present invention. The examples are offered for illustrative purposes only, and are not intended to limit the scope of the present invention in any way.

EXAMPLES

Example 1

Time Course Evaluation of Virus Compatibility

A CMV-β-gal adenovirus (i.e., an adenoviral vector driven by a CMV (cytomegalovirus) promoter and encoding a β-galactosidase (β-gal) reporter gene) was used as a stock virus in this example.

Stock virus having a viral titer of $3 \times 10^7$ (also referred to herein as 3x10^7 or 3E+07) plaque-forming units/ml (pfu/ml) was incubated in catheters at 37° C. The catheters used were endocardial catheters like those described in international patent application WO/9922655, the disclosure of which is hereby incorporated by reference in its entirety. These catheters have a proximal portion formed from heat-treated stainless steel and a distal portion formed from a nitinol hypotube (referred to in these examples as "catheter" or "injection catheter" or "needle injection catheter"); the hub is comprised of polycarbonate. After the allotted amount of time (0–30 minutes, where 0 minutes refers to the situation in which the viral solution was flushed through the catheter), the viral solution was pushed through the catheter into a polypropylene eppendorf tube. The viral solution was then titered on HeLa cells (human epidermoid carcinoma cells). For this purpose, HeLa cells were first plated out in well plates at 70% confluency the day before the experiment. Prior to contacting the HeLa cells, the viral solution was diluted appropriately in infection media (DMEM (Dulbecco's Modified Eagle's Medium)+2% FBS (Fetal Bovine Serum)) to achieve a result of 1E+02–1E+03 infected cells per well. The diluted virus was added to the HeLa cells in the wells and incubated at 37° C. for 1 hour. 5 mls of DMEM +10% FBS were then added to each well, followed by incubation for 24–30 hours at 37° C. After aspirating of the media, the cells were fixed in 0.5% glutaraldehyde in PBS (phosphate buffered saline) for 10 minutes. The cells were washed twice in PBS and stained using an X-gal staining solution overnight at 37° C. (X-gal is 5-bromo4-chloro-3-indolyl-β-D-galactoside, which is hydrolyzed by β-galactosidase to form a blue product). Blue cells were counted the next day to determine the titer.

Data are presented in the table to follow for 0 (simple flush through), 5, 10 and 30 minutes in the catheter. The data are presented in the table in terms of cell counts (accounting appropriately for dilution), in terms of absolute titer (pfu/ml), and in terms of percentage of the titer of stock virus (3.0E+07 pfu/ml).

Figure 1:
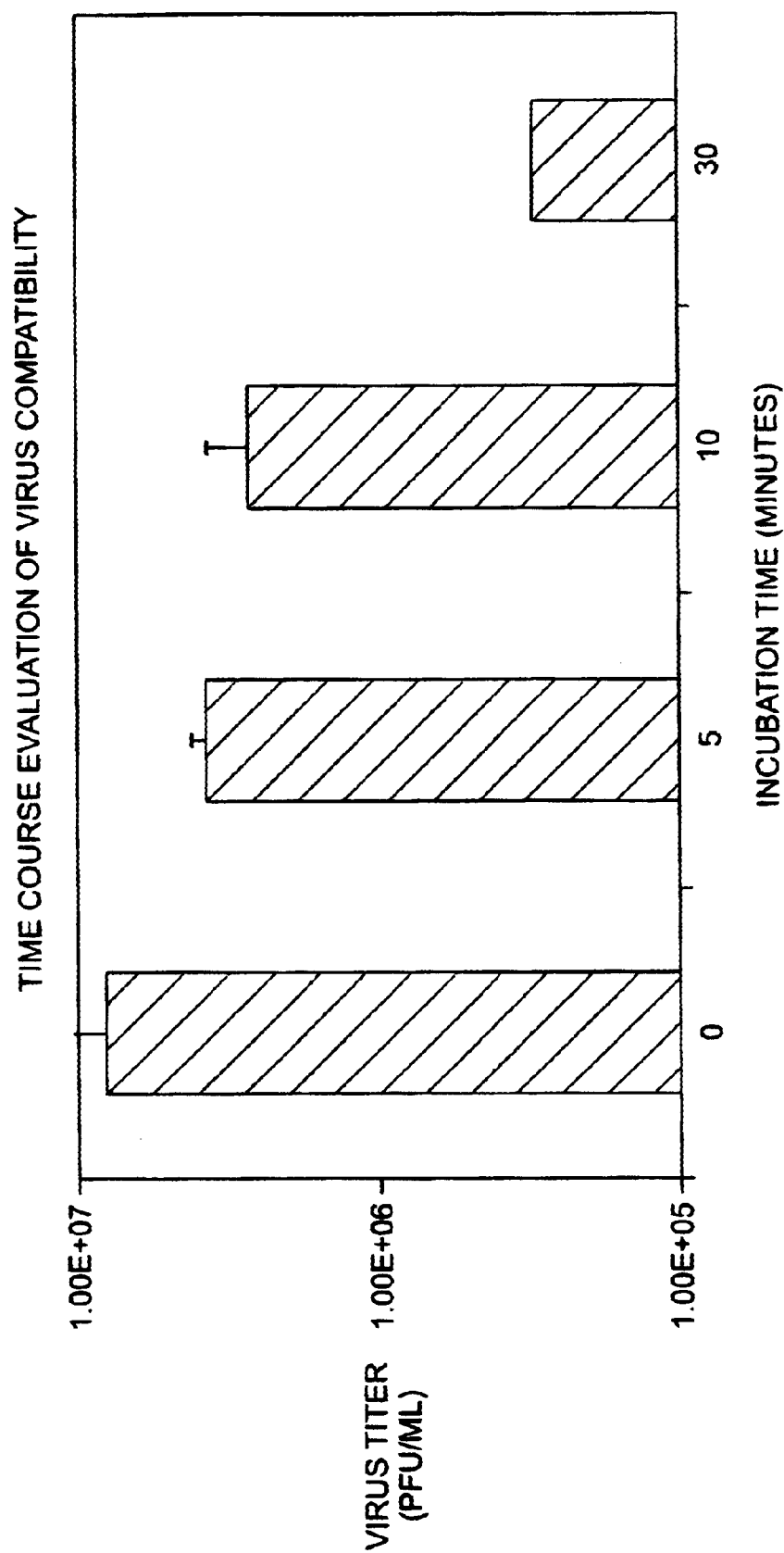
FIG. 1 presents absolute virus titer (log scale) as a function of time for an untreated injection catheter.
Figure 2:
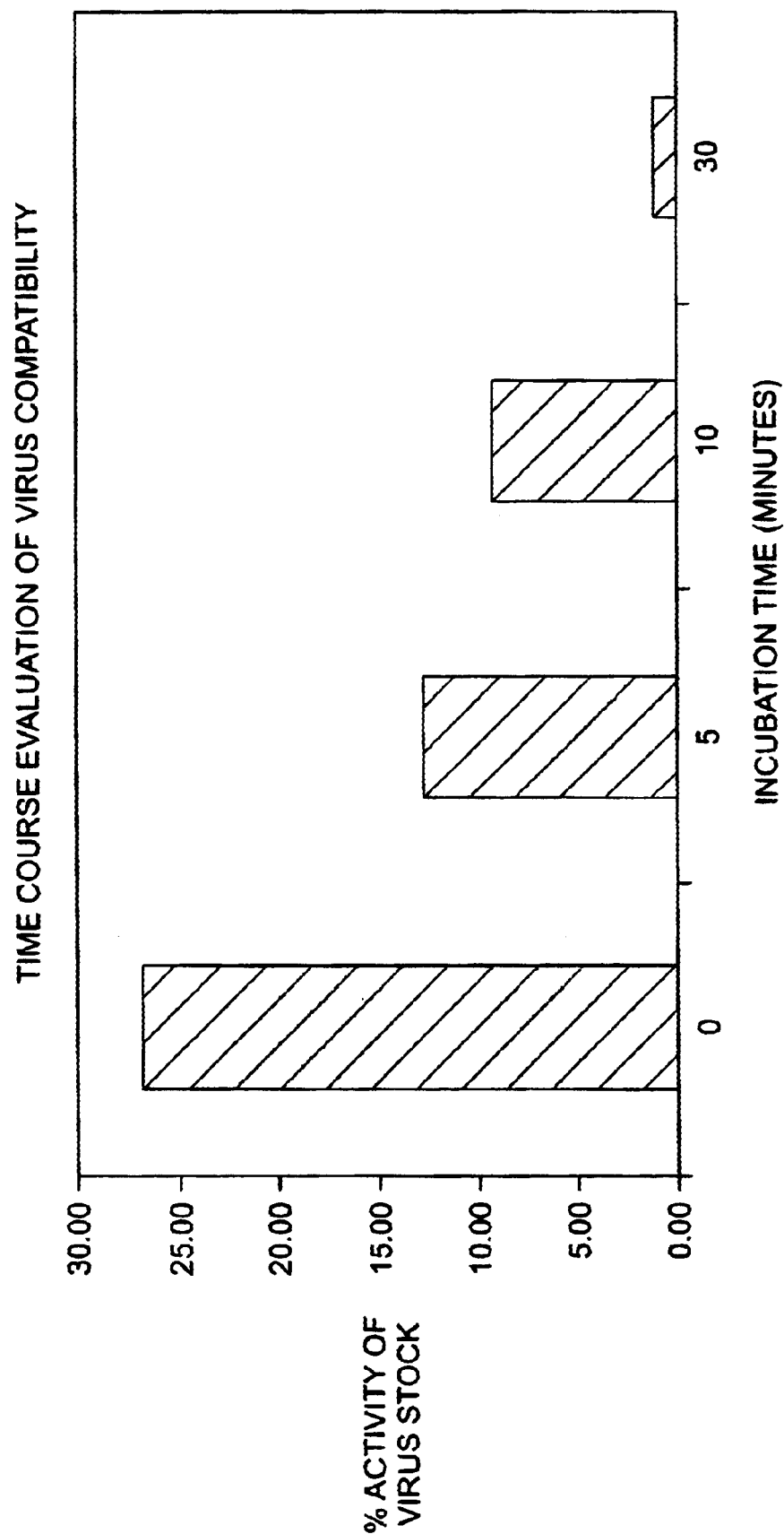
FIG. 2 presents the data of FIG. 1 as a percentage of viral stock titer (linear scale).

FIG. 1 presents these data in terms of absolute virus titer (log scale) and FIG. 2 presents these data relative to the viral stock titer (linear scale). These data suggest that residency in the catheter results in a deterioration of viral efficacy and that this incompatibility effect increases with increasing exposure time.

| Time (min.) | Pos. Cells #1 | Pos. Cells #2 | Pos. Cells #3 | Titer (pfu/ml) | Std. Dev. | % of stock |
|---|---|---|---|---|---|---|
| 0 | 7400000 | 10800000 | 5900000 | 8.03E+06 | 2.51E+06 | 26.78 |
| 5 | 3400000 | 4100000 | | 3.75E+06 | 4.95E+05 | 12.50 |
| 10 | 3900000 | 2400000 | 1800000 | 2.70E+06 | 1.08E+06 | 9.00 |
| 30 | 300000 | 300000 | 300000 | 3.00E+05 | 0.00E+00 | 1.00 |

Example 2

Time Course Evaluation of Virus Compatibility

Procedures similar to Example 1 were followed, except that an additional initial viral titer (4E+08 pfu/ml) was examined, both in a catheter and as a control. For the control, the virus was exposed to a polypropylene vial for the appropriate period.

The number of positive cells was counted:

(a) after 0 (flush through) and 30 minutes in the control vial (4E+08 pfu/ml), (b) after 0 (flush through) and 30 minutes in the catheter, using the same stock virus titer as the control (4E+08 pfu/ml), and (c) after 0 (flush through) and 30 minutes in the catheter, using a lower stock virus titer (3E+07 pfu/ml).

Figure 3:
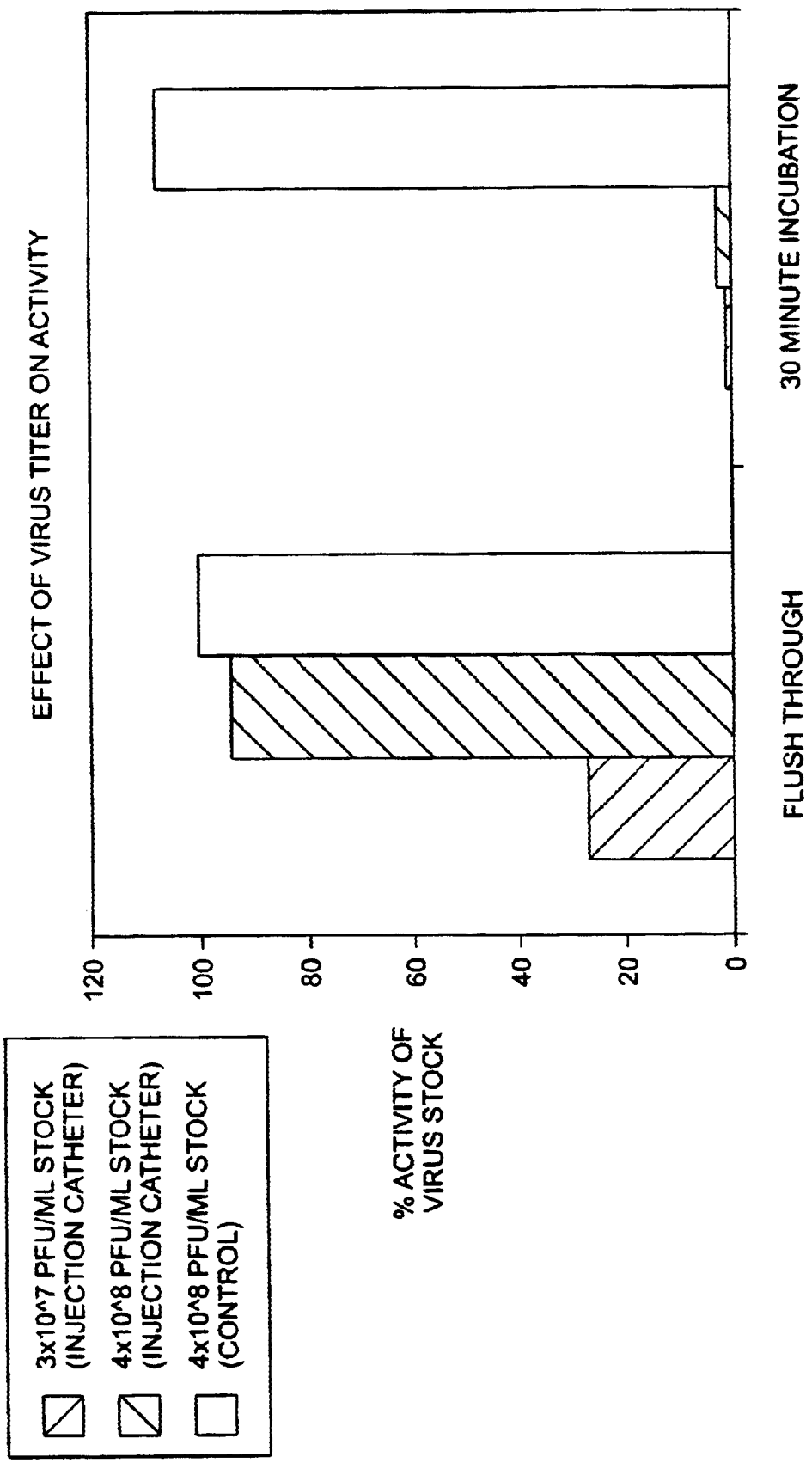
FIG. 3 presents virus titer (as a percentage of virus stock titer): (a) after 0 (flush through) and 30 minutes for a control (4E+08 pfu/ml initial titer), (b) after 0 (flush through) and 30 minutes for an injection catheter constructed of stainless steel and nitinol, using the same stock virus titer as the control (4E+08 pfu/ml initial titer), and (c) after 0 (flush through) and 30 minutes for an injection catheter constructed of stainless steel and nitinol, using a lower stock virus titer (3E+07 pfu/ml initial titer).

Data are presented in FIG. 3, which presents these data as a percentage of viral stock titer. As in Example 1, there is a significant drop in virus activity as a function of incubation time. For a virus stock titer of 3E+07 pfu/ml, a flush through resulted in a 75% loss of activity relative to the viral stock while a 30-minute incubation resulted in a 99% loss of activity. At the higher titer of virus, 4E+08 pfu/ml, a flush through the catheter resulted in only a 6% loss of activity.

However, 97% activity was lost after 30 minutes, consistent with the results at the lower titer. Hence, simply increasing viral titer may not appear to be an effective solution to the loss in viral efficacy observed.

Example 3

Time Course Evaluation

Figure 4:
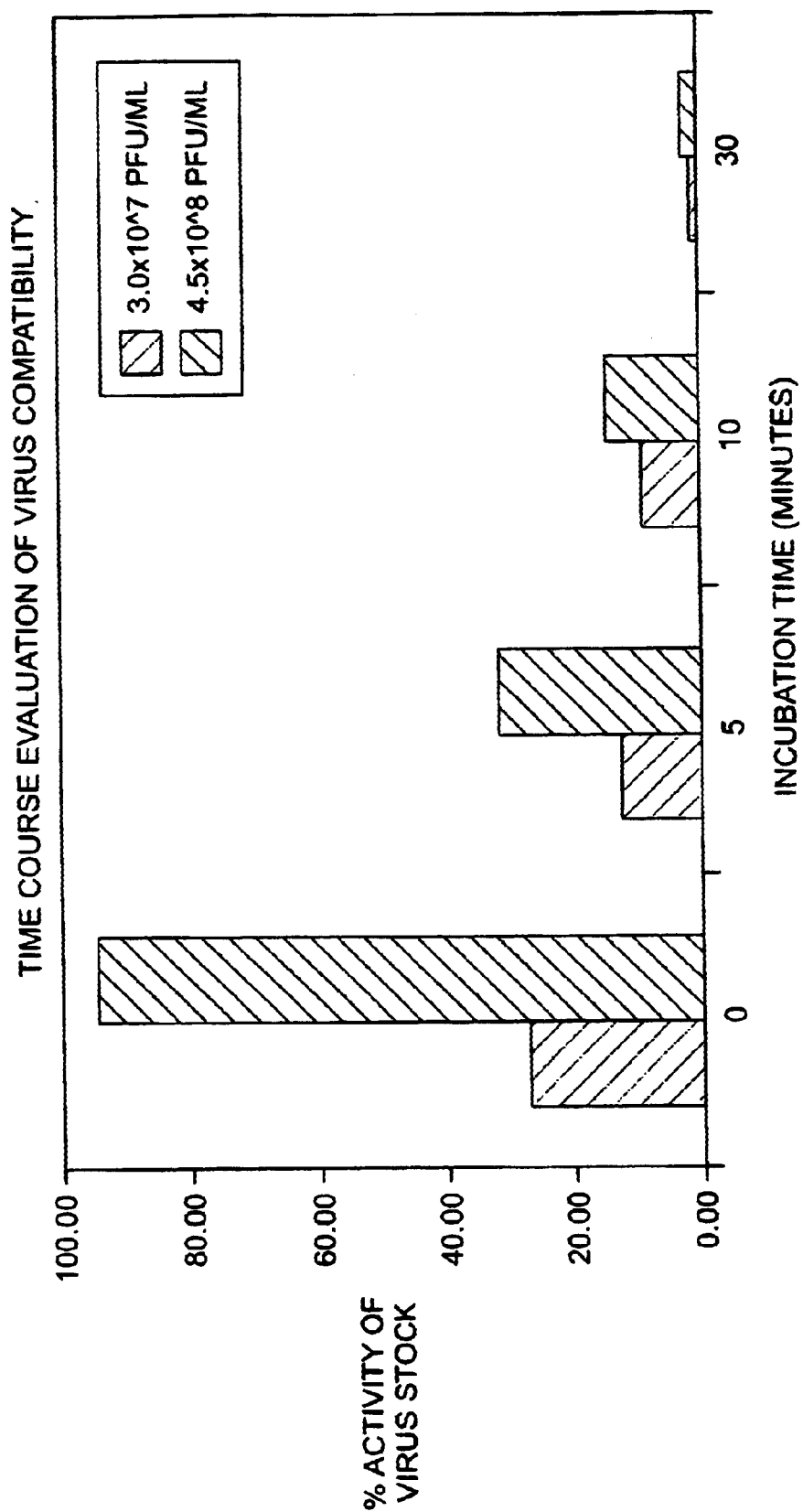
FIG. 4 presents virus titer (as a percentage of virus stock titer) after 0 (flush through), 5, 10 and 30 minutes an injection catheter constructed of stainless steel and nitinol for two viral solutions (3.0E+7 pfu/ml and 4.5E+8 pfu/ml initial titer).

Procedures similar to Examples 1 and 2 were followed for viral solutions having titers of 3.0E+7 pfu/ml and 4.5E+8 pfu/ml. Positive cells were counted after 0 (flush through), 5, 10 and 30 minutes in the catheter. Data are presented in FIG. 4, which shows a more pronounced drop in activity for the lower concentration over shorter incubation times. This difference, however, becomes less significant at longer incubation times, as also seen in Example 2.

Example 4

Material Compatibility

In this example, the procedures of Example 1 were followed, except viral titers were measured after exposure to various materials for 30 minutes. In some examples, a stock viral titer of 5E+08 was used. In others (namely, the second control, the injection catheter, and the passivated injection catheter), a stock viral titer of 4E+08 was used. For a control, the stock virus was placed in a polypropylene vial for 30 minutes.

The lumen materials for this example have a proximal portion approximately 48" in length and a distal portion measuring approximately 14" in length. The overall length is slightly less than 62", because the distal end is inserted into the proximal end. (Note that Groups #3 and #4 below were single pieces of 5 ft. lengths.)

Lumen materials for this example were as follows (dimensions are in inches if not otherwise indicated):

(1) injection catheter with a proximal end (0.013"×0.025") formed from heat-treated stainless steel, a distal end (0.009"×0.014") formed from a nitinol hypotube, and containing polycarbonate hub (See Example 1 above);

(2) 0.013×0.025 stainless steel hypotube (proximal end) swaged to a 0.007×0.014 stainless steel hypotube (distal end);

(3) 0.0093×0.014 nitinol hypotube;

(4) 0.010×0.018 stainless steel hypotube;

(5) 0.013×0.025 stainless steel hypotube (proximal end) and 0.0093×0.014 nitinol hypotube (distal end); the nitinol was insulated the with a small piece of 0.013×0.024 Cristamid MS1100 (semiaromatic polyamide; Elf Atochem), the larger stainless steel hypotube collar was bonded over the joint; the proximal stainless steel hypotube was not allowed to touch the distal length of nitinol;

(6) full length HDPE necked to 0.010×0.015 on the distal end and 0.013×0.025 on the proximal end;

(7) injection catheter of group #1, with passivation treatment.

The passivation process was conducted as set forth in ASTM standard A967-96 "Chemical passivation of stainless steel parts". Specifically, the catheter was treated with a 7% weight to volume citric acid solution in water for 7 minutes at 70° C. Immediately after removal from the citric acid solution, the catheter was thoroughly rinsed in water multiple times.

Figure 5:
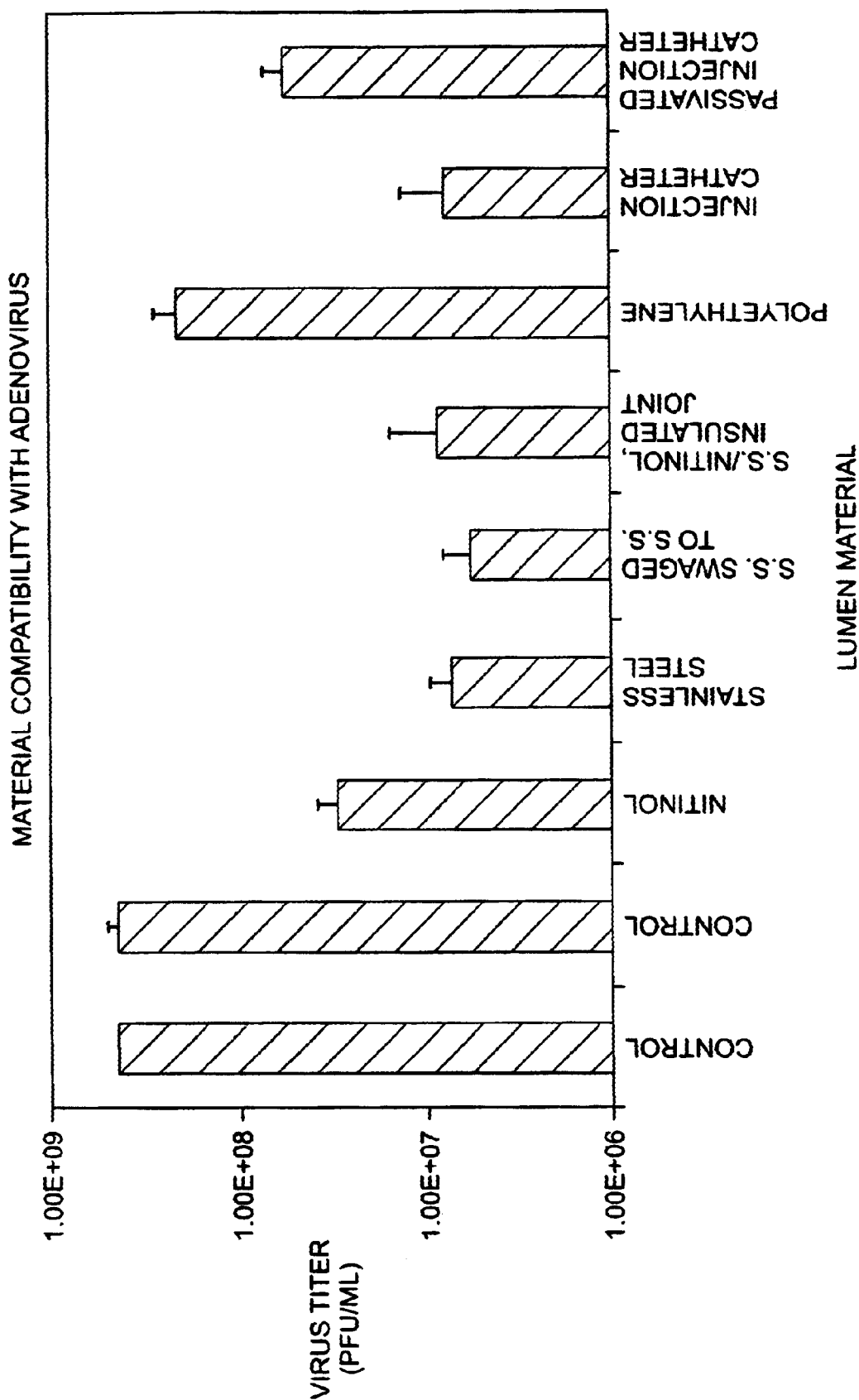
FIG. 5 presents absolute virus titer (log scale) after 30 minute incubation in the following materials: a nitinol lumen, a stainless steel lumen, a lumen of stainless steel swaged to nitinol, a lumen of stainless steel swaged to nitinol with an insulated joint, a polyethylene lumen, an injection catheter constructed of stainless steel and nitinol, and a passivated injection catheter constructed of stainless steel and nitinol.
Figure 6:
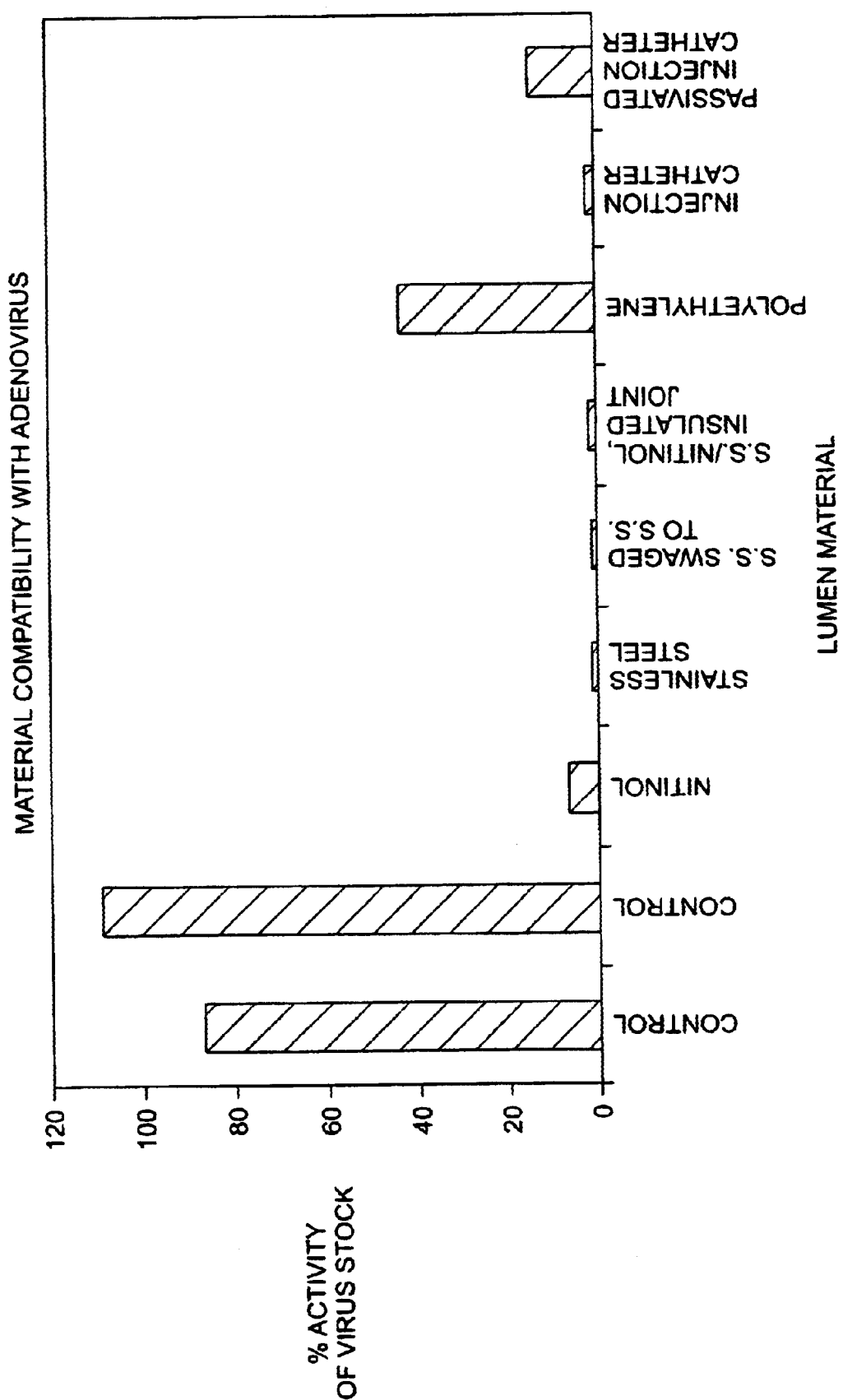
FIG. 6 presents the data of FIG. 5 as a percentage of viral stock titer (linear scale).
Figure 7:
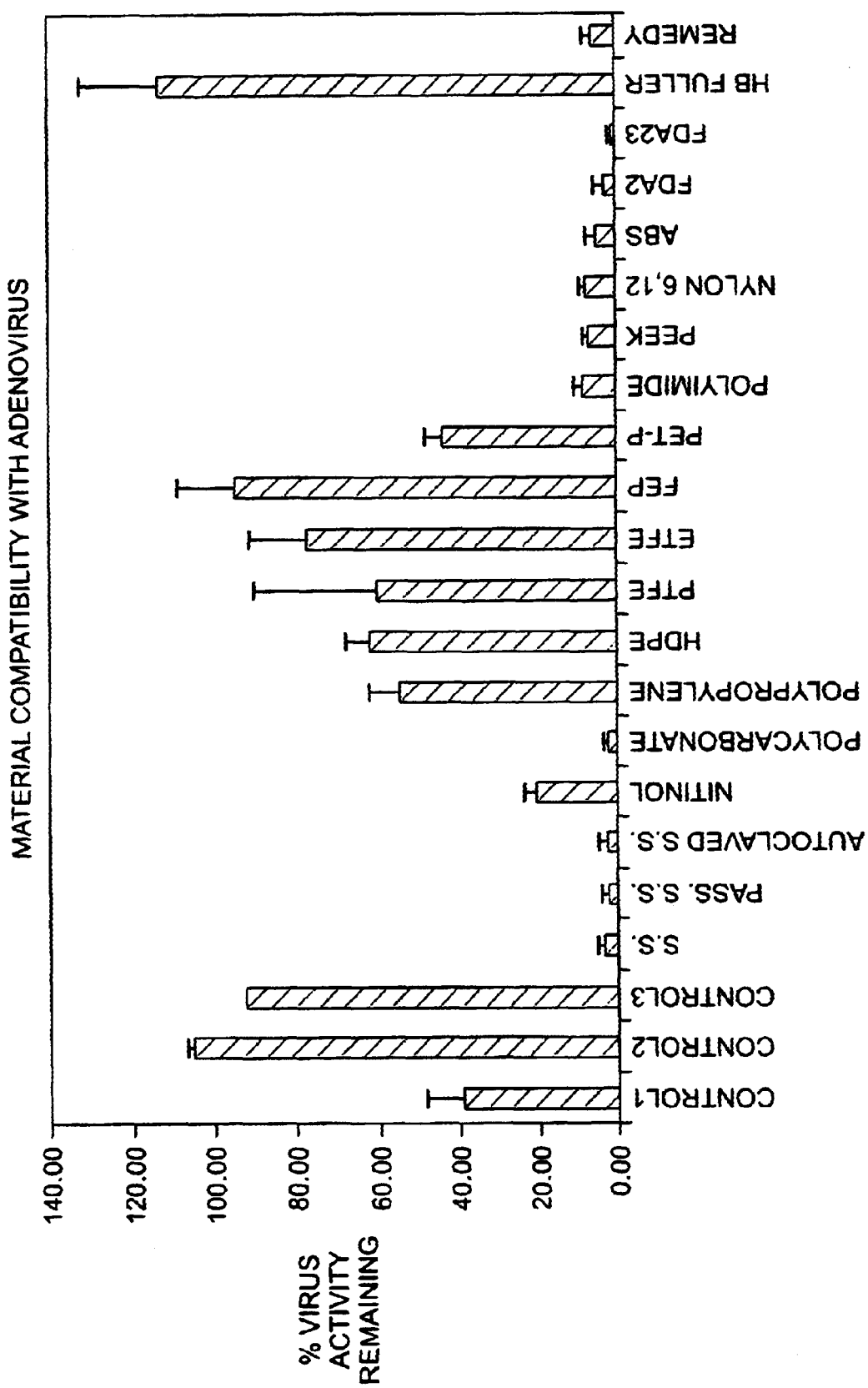
FIG. 7 presents virus titer as a percentage of viral stock titer (linear scale) after 30 minute incubation in connection with the following materials: stainless steel, passivated stainless steel, autoclaved stainless steel, nitinol, polycarbonate, polypropylene, high density polyethylene (HDPE), polytetrafluoroethylene (PTFE), modified ethylene-tetrafluoroethylene copolymer (ETFE), poly (tetrafluoroethylene-co-hexafluoropropene) (FEP), polyethylene terephthalate polyester (PET-P), polyimide, poly ether ether ketone (PEEK), nylon 6/12, acrylonitrile/butadiene/styrene resin (ABS), FDA2, FDA23, HP Fuller, and a REMEDY infusion balloon catheter.
Figure 8:
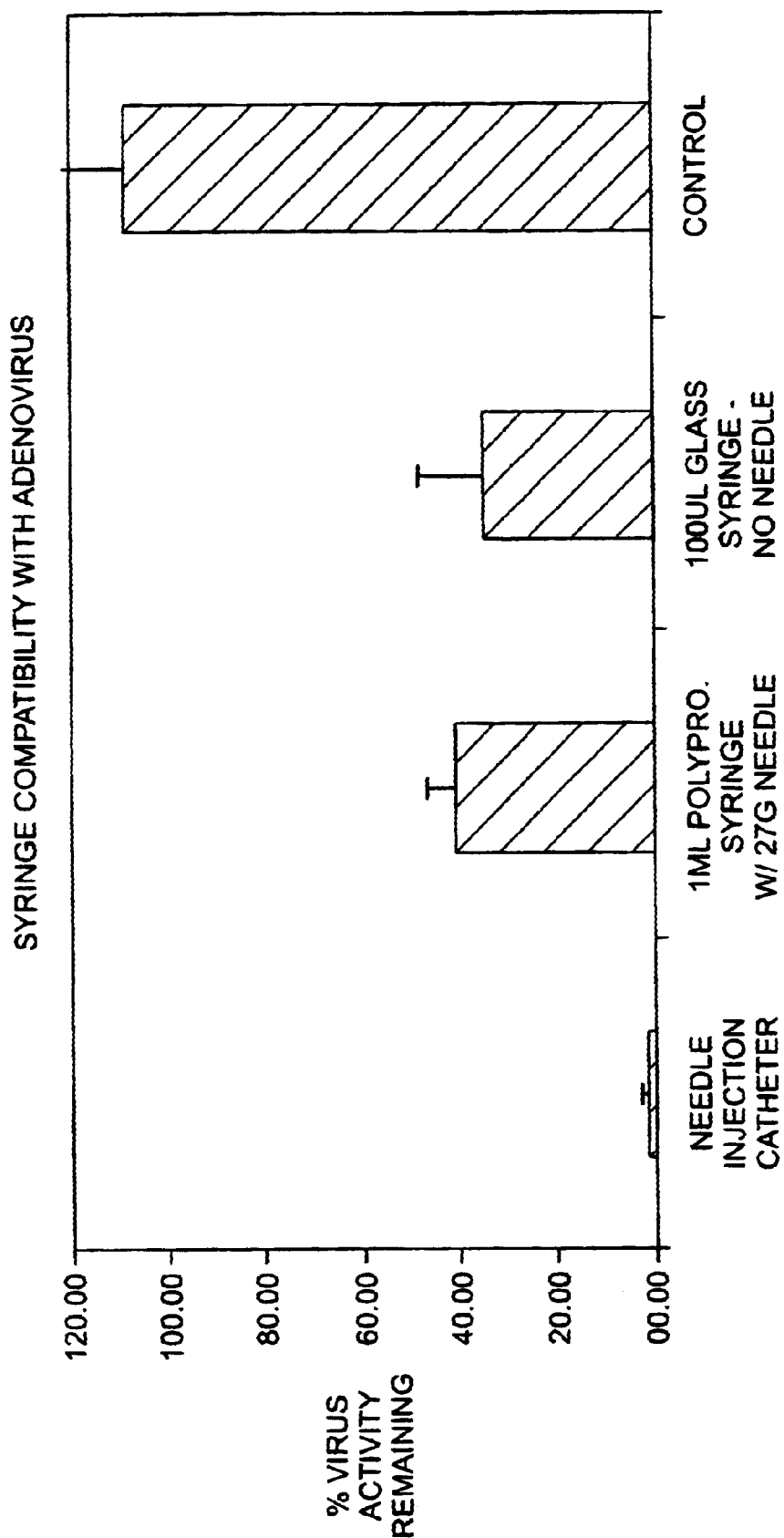
FIG. 8 presents virus titer as a percentage of viral stock titer (linear scale) after 30 minute incubation within a needle injection catheter, a polypropylene syringe (with needle), a glass syringe (without needle) and a control.
Figure 9:
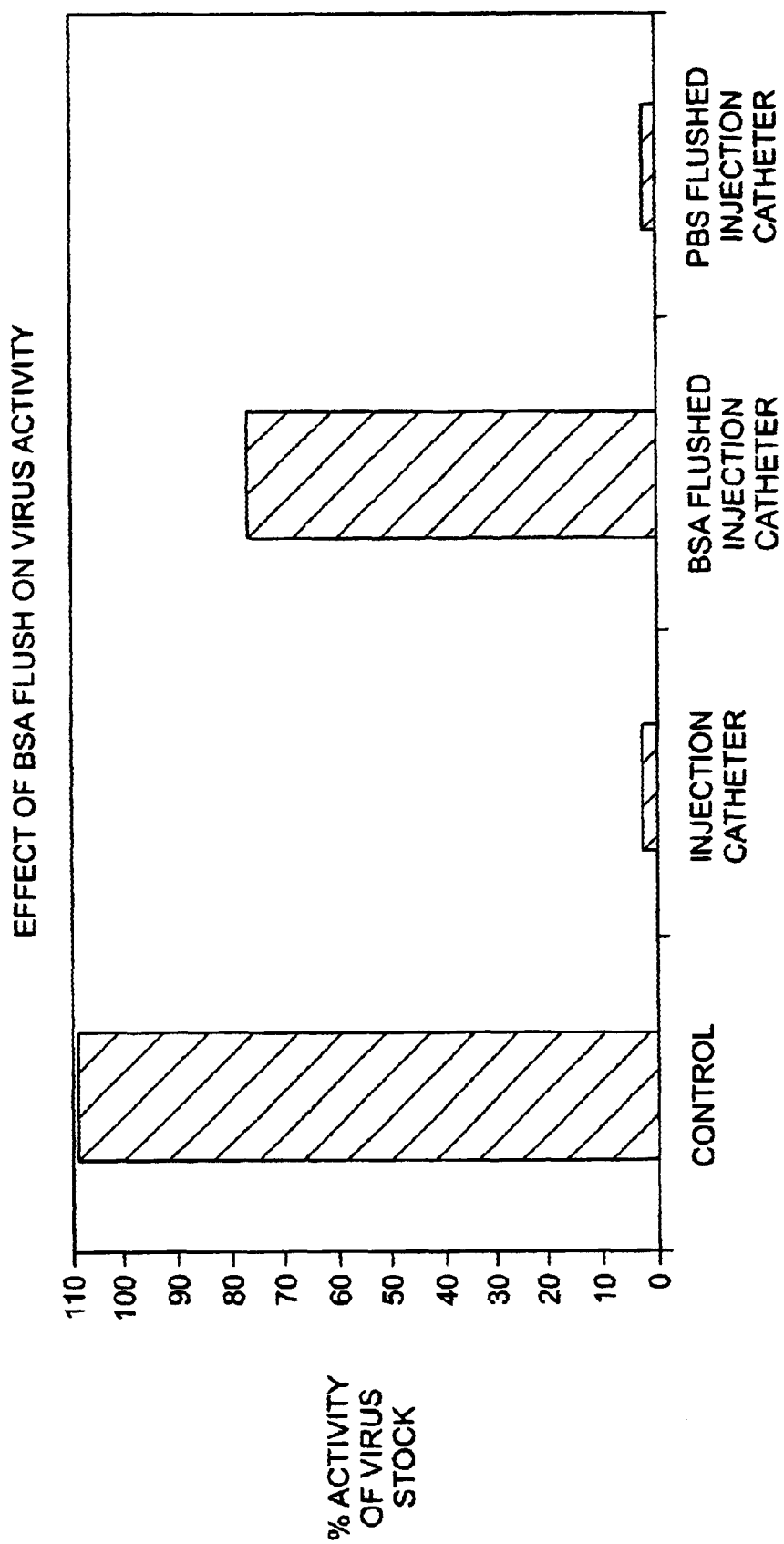
FIG. 9 presents virus titer as a percentage of viral stock titer (linear scale) after 30 minute incubation within a control vial, an untreated needle injection catheter, a needle injection treated flushed with BSA and a needle injection catheter treated with PBS. The BSA- and PBS-treated catheters were provided by flushing with BSA and PBS solutions prior to incubation with virus.

Absolute titers are presented in FIG. 5 (log scale), and titer as a percentage of viral stock are presented in FIG. 6 (linear scale). These data suggest that all of the lumen materials tested had a negative effect on viral efficacy.

In particular, all untreated lumens containing stainless steel (stainless steel per se, stainless steel swaged to nitinol, stainless steel swaged to nitinol with insulated joint and injection catheter) reduced virus activity to only 1–2% of the stock virus titer. Similarly, virus incubated in nitinol retained only 6% of its original activity. Virus incubated within the passivated injection catheter retained 15% of its original activity. 50% of the virus activity was lost post incubation in the polyethylene lumen.

These data suggest that certain metals, such as stainless steel and nitinol, result in substantial loss of viral efficacy as compared to certain polymers, such as polypropylene (control) and polyethylene. The presence of flow in the polymeric and metal lumens versus the lack of flow in the control sample may have negatively impacted virus activity in addition to a detrimental effect as a result of the high surface area to volume ratio with the lumen samples.

Figure 10:
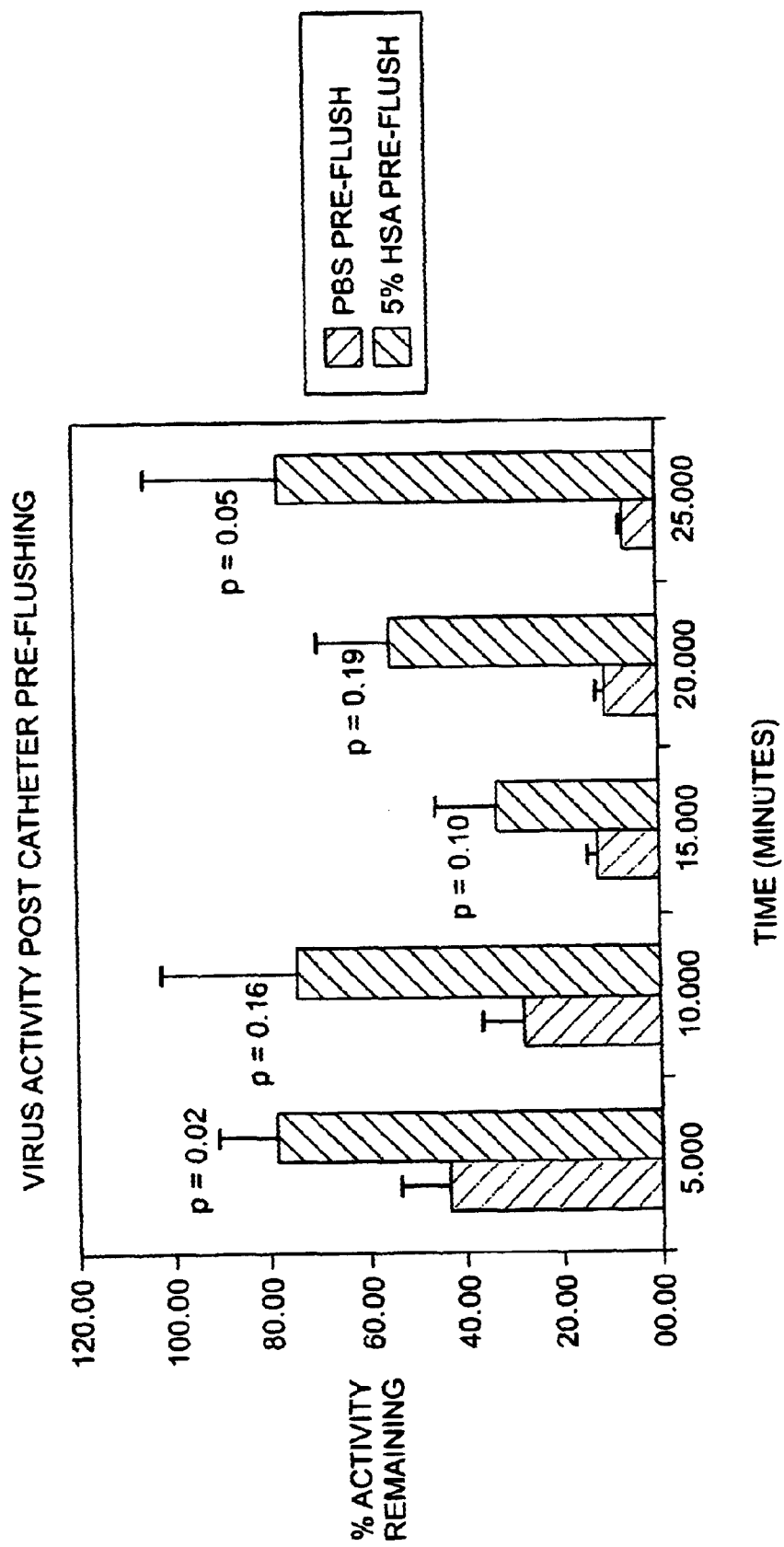
FIG. 10 presents virus titer as a percentage of viral stock titer (linear scale) for needle injection catheters pre-flushed with 5% HSA solution and PBS solution.

Moreover, these data suggest that metal can be passivated by proper chemical treatment. Without wishing to be held to any particular theory, it is believed that the citric acid solution acts to remove free iron and iron oxides and to build up a surface layer comprised primarily of chromium oxides. The resulting surface is non-electrochemically active and is believed to be relatively inert to other chemical and physico-chemical interactions.

It is known that joints between dissimilar metals can create a galvanic reaction in the presence of an electrolyte, resulting in the release of free metal ions and that this may be prevented by insulating the joint between the two metals. Hence, these data also suggest that the loss in efficacy seen with lumens having stainless steel/nitinol joints is not due to a galvanic interaction between nitinol and stainless steel, since the data for insulated and uninsulated joints did not statistically differ.

Example 5

Material Compatibility With Adenovirus

In this Example, viral solution, titer=$4.8\times10^8$ pfu/ml, was incubated with a ⅜ inch diameter×1 inch long cylindrical material sample for 30 minutes at 37° C. in polypropylene tubes. The control was virus placed in a polypropylene tube without a material sample. The activity of the virus was assessed after the 30 minute incubation period. The results are shown in FIG. 7 and also include a 30 minute incubation within a REMEDY infusion balloon catheter.

Polymeric materials found to be incompatible with virus include LEXAN polycarbonate (available from General Electric), polyimide (VESPEL SP-1; DuPont), poly ether ether ketone (PEEK) (KETRON; DSM Engineering Plastic Products), nylon 6/12 (Poly Penco), and acrylonitrile/butadiene/styrene resin.

Polymeric materials that appear to be more virus compatible include polypropylene, high density polyethylene (HDPE), virgin polytetrafluoroethylene (PTFE), modified ethylene-tetrafluoroethylene copolymer (ETFE) (TEFZEL; DuPont) and poly(tetrafluoroethylene-co-hexafluoropropene)(FEP) (FEP 100; DuPont). Polyethylene terephthalate polyester (PET-P) (ERTALYTE; DSM Engineering Plastic Products) was also more compatible.

Consistent with FIGS. 5 and 6, virus activity dropped significantly in the presence of stainless steel (type 304). The nitinol tested in FIGS. 5 and 6 (available from Raychem Corp. and composed of 55.8% nickel with a balance of titanium) was tested as a catheter including a polycarbonate manifold. Since polycarbonate has been found to be incompatible with virus, the compatibility of Nitinol was uncertain from FIGS. 5 and 6. FIG. 7 indicates that Nitinol is more compatible than stainless steel at 20% activity retained after a 30-minute incubation. However, it is less compatible (statistically significant) than the more compatible polymers apart from PTFE. Nonetheless, PTFE, being a fluoropolymer, is expected to be significantly better than Nitinol in a larger sampling.

Among adhesives, HB Fuller 3507 (a urethane-based adhesive available from HB Fuller) was found to be more compatible with virus than FDA2 or FDA23 (epoxy-based adhesives available from Tracon).

Virus incubated within the REMEDY catheter, an infusion balloon catheter available from Boston Scientific Corporation, Natick, Mass., retained only 5% virus activity, consistent with the fact that this catheter contains a polyimide shaft material.

Example 6

Syringe Compatibility With Adenovirus

Virus solution, initial titer=$4.5\times10^8$ pfu/ml, was incubated within a needle injection catheter like that of Example 1, within a 1 ml polypropylene syringe with a 27 g needle attached (similar to those commonly used in epicardial injections) and within a 100 $\mu$l glass syringe without an attached needle. The control is a polypropylene tube. The results are shown in FIG. 8. This experiment indicates that the glass syringe is comparable to polypropylene, with about 40% virus activity remaining after a 30 minute incubation. Also, virus injection from conventional needle/ polypropylene syringe assemblies also result in a reduction of virus activity, potentially due in part to the stainless steel needle.

Example 7

Effect of BSA and PBS Flush on Viral Efficacy

Viral solution (initial titer $5.5\times10^8$) was incubated in a control vial, an untreated needle injection catheter (like that of Example 1), a needle injection catheter treated with BSA (bovine serum albumin) and a needle injection catheter treated with phosphate-buffered saline (PBS). The BSA-treated catheter was provided by flushing a catheter with a 1% aqueous solution of BSA prior to incubation with virus. The PBS treated catheter was similarly flushed with PBS. The stock virus titer for this example was 5.5E+08 pfu/ml and the incubation time was 30 minutes.

Data are presented in FIG. 9 as a percentage of virus stock titer (linear scale). Virus incubated in the BSA-treated catheter retained 76% of its efficacy, compared to sharp drop in efficacy for the untreated and PBS-treated catheters.

These data suggest that a reduction in viral efficacy in the catheter can be substantially diminished by treatment with BSA. Without wishing to be held to any theory, the albumin may provide a barrier between the metal and virus. Alternatively, dissolved albumin may have a stabilizing effect on the virus in suspension. Therefore, the addition of albumin directly to the virus formulation would be expected to exert a similar effect. The resulting effect would be dependent on the concentration of albumin added to the formulation. These effects are explored in Example 9 below.

Example 8

Effect of HSA and PBS on Virus Activity

A 5% solution of HSA (human serum albumin) (U.S.P. Albutein 5% Solution, made by Alpha Therapeutic Corporation in Los Angeles, Calif.) was pre-flushed through a needle injection catheter like that of Example 1 prior to virus incubation. Initial viral titer was $5\times10^8$ pfu/ml. The catheters were filled, and 50 µl of virus was pushed out of each catheter and assayed after 5 minutes. Additional 50 µl volumes were pushed out every 5 minutes. Since the dead space in the catheter is ~150–160 µl and since the catheter design does not promote back-mixing, one would expect a decrease in virus activity over the first 15 minutes ($1^{st}$ injection resided in the catheter for 5 minutes, $2^{nd}$ injection resided 10 minutes and $3^{rd}$ resided 15 minutes) and a leveling off between 15 and 25 minutes ($3^{rd}$ through $5^{th}$ injections resided in the catheter for a total of approximately 15 minutes). FIG. 10 indicates that a PBS pre-flush does not exert a protective effect on the virus, consistent with the results of the previous example. Additionally, the expected trend as a function of time is indeed observed for the PBS. The HSA pre-flush, however, does preserve virus activity relative to the PBS pre-flush. The protective effect of HSA is sustained through all 5 injections.

Example 9

Effect of HSA Added to Adenovirus Suspension

A 5% solution of HSA (human serum albumin) (U.S.P. Albutein 5% Solution, made by Alpha Therapeutic Corporation in Los Angeles, Calif.) was added to an adenoviral suspension containing $5\times10^8$ pfu/ml virus to achieve total HSA concentrations of 0% (no addition), 0.005% and 0.1%, and these suspensions were incubated within a needle injection catheter like that of Example 1 for 30 minutes. The solution was removed and the activity of the adenovirus was assayed. The results are presented in FIG. 11, which demonstrates that the addition of HSA directly to the virus suspension has a concentration-dependent protective effect on adenovirus activity. Adenovirus in a solution of 0.1% HSA has a significantly greater activity (82%) post incubation within the catheter relative to adenovirus without added HSA (1.6%).

Example 10

Viral Adsorption Study

In this example, OD 260 (optical density at a wavelength of 260 nm) data were taken for stock virus, stock virus after 1:10 dilution in PBS, stock virus after flushing it though an injection catheter, stock virus after incubation in an injection catheter for 30 minutes, and stock virus after incubation in polyethylene (high density) for 30 minutes. Stock virus titer in this example was 1E+09 pfu/ml.

OD 260 provides data related to viral concentration, which data is independent of its biological activity. OD 260 data for the virus stock (1E+09 pfu/ml) without exposure to the catheter (control), after flushing through the catheter, and after an incubation time of 30 minutes in the catheter are presented in FIG. 12. These data suggest that the concentration of viral particles is effectively the same for samples unexposed to the injection catheter, exposed to the injection catheter during the brief flush-through procedure and exposed to the injection catheter for 30 minutes. These data, in combination with data from the examples above, suggest that the catheter does not retain appreciable amounts of virus, in some fashion (e.g., by adsorption), but rather acts predominantly to inactive the virus. (FIG. 13 includes an absorbance value for a 1:10 dilution of the stock virus, indicating the sensitivity of the method.)

OD 260 data for virus stock (1E+09 pfu/ml), for the virus stock at 1:10 dilution (1E+08 pfu/ml), and for the virus stock after incubation in polyethylene for minutes are presented in FIG. 13. As expected, the OD 260 after a 1:10 dilution of the virus stock is on the order of one-tenth that of the undiluted virus stock, according to Beer's Law. Moreover, the differences between the OD 260 of the virus stock and the virus stock after 30 minutes in polyethylene, while different, do not appear to be statistically different. These data, in combination with data from the examples above, suggest that polyethylene may retain virus (e.g., by adsorption), but predominantly acts to inactivate the virus.

The present invention provides methods and devices for the delivery of pharmaceutically active materials that overcome incompatibility problems of the prior art. Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

We claim:

1. A modified medical device for delivery of a pharmaceutically active material comprising:
    a catheter comprising an incompatible metallic delivery lumen which acts to substantially reduce pharmaceutical effectiveness of said pharmaceutically active material upon contact with said pharmaceutically active material;
    wherein said incompatible metallic delivery lumen is modified by providing it with a layer of polymeric material such that said substantial reduction in the pharmaceutical effectiveness or the pharmaceutically active material is diminished upon contact with said drug delivery lumen.

2. The modified medical device of claim 1, wherein said catheter is an intravascular catheter.

3. The modified medical device of claim 2, wherein said intravascular catheter is an injection catheter.

4. The modified medical device of claim 2, wherein said intravascular catheter is a percutaneous myocardial revascularization catheter.

5. The modified medical device of claim 2, wherein said metallic lumen comprises stainless steel or nitinol.

6. The modified medical device of claim 1, wherein said metallic lumen comprises stainless steel or nitinol.

7. The modified medical device of claim 1, wherein said polymeric material comprises a pharmaceutically acceptable natural polymer.

8. The modified medical device of claim 7, wherein said natural polymer is a protein.

9. The modified medical device of claim 1, wherein said polymeric material comprises a synthetic polymer.

10. The modified medical device of claim 9, wherein said synthetic polymer is selected from a polyalkylene and a fluorocarbon polymer.

11. The modified medical device of claim 10, wherein said synthetic polymer is selected from low density polyethylene, high density polyethylene, polypropylene, polytetrafluoroethylene, poly(tetrafluoroethylene-co-hexafluoropropene), modified ethylene-tetrafluoroethylene copolymer, ethylene chlorotrifluoroethylene copolymer and polyvinylidene fluoride.

12. The modified medical device of claim 9, wherein said polymeric material is provided by coating the incompatible metallic or polymeric lumen with uncured polymer, and curing said uncured polymer.

13. The modified medical device of claim 12, wherein said polymer is a silicone resin.

14. The modified medical device of claim 9, wherein said polymeric material is provided in the form of a preformed tube.

15. The modified medical device of claim 8, wherein said protein is albumin.

16. The modified medical device of claim 7, wherein the natural polymer is elected from hyaluronic acid, laminin, fibronectin, fibrin, collagen dextran, dextran sulfate and heparin.

17. The modified medical device of claim 7, wherein said natural polymer is a polysaccharide.

18. The modified medical device of claim 1, further comprising said pharmaceutically active material, wherein said pharmaceutically active material comprises an agent selected from the group consisting of polynucleotides, proteins, small molecule drugs and large molecule drugs.

19. The modified medical device of claim 1, wherein said intravascular catheter is a transmyocardial revascularization catheter.

20. The modified medical device of claim 1, further comprising said pharmaceutically active material, wherein said pharmaceutically active material comprises a virus or virus-like particles.

21. The modified medical device of claim 9, wherein said more compatible synthetic polymer is a polyether block amide.

22. The modified medical device of claim 9, wherein said more compatible synthetic polymer is a silicone polymer.

23. The modified medical device of claim 9, wherein said more compatible synthetic polymer is polypropylene.

24. The modified medical device of claim 1, further comprising said pharmaceutically active material, wherein the pharmaceutically active material comprises a polynucleotide.

25. The modified medical device of claim 24, wherein the pharmaceutically active material comprises naked DNA.

26. The modified medical device of claim 24, wherein the pharmaceutically active material comprises a viral vector.

27. The modified medical device of claim 26, wherein the viral vector is an adenoviral vector.

28. The modified medical device of claim 24, wherein the pharmaceutically active material comprises a non-viral vector.

29. The modified medical device of claim 1, further comprising said pharmaceutically active material, wherein the pharmaceutically active material comprises a protein.

30. The modified medical device of claim 1, wherein the incompatible metallic or polymeric lumen comprises dissimilar metal.

31. The modified medical device of claim 30, wherein the layer of more compatible material is a polymeric layer that comprises a synthetic polymer.

32. The modified medical device of claim 30, wherein the dissimilar metals comprise stainless steel and nitinol.

33. The modified medical device of claim 31, wherein the catheter is an injection catheter.

34. The modified medical device of claim 31, further comprising said pharmaceutically active material, wherein the pharmaceutically active material comprises a viral vector.

* * * * *

UNITED STATES PATENT AND TRADEMARK OFFICE
CERTIFICATE OF CORRECTION

PATENT NO. : 6,663,606 B1
DATED : December 16, 2003
INVENTOR(S) : Barry et al.

It is certified that error appears in the above-identified patent and that said Letters Patent is hereby corrected as shown below:

<u>Title page,</u>
Item [75], Inventors, delete ";Brian Berg, St. Paul, MN (US); Justin Crank, Minneapolis, MN (US)".

<u>Column 17,</u>
Line 19, change "elected" to -- selected --.

<u>Column 18,</u>
Line 26, change "metal" to -- metals --.

Signed and Sealed this

First Day of June, 2004

JON W. DUDAS
*Acting Director of the United States Patent and Trademark Office*